United States Patent
Habermann et al.

(10) Patent No.: US 7,455,987 B1
(45) Date of Patent: Nov. 25, 2008

(54) **SIGNAL SEQUENCES FOR PREPARING LEU-HIRUDIN BY SECRETION BY *E. COLI* INTO THE CULTURE MEDIUM**

(75) Inventors: Paul Habermann, Eppstein (DE); Rudolf Bender, Bad Soden (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 737 days.

(21) Appl. No.: 09/664,326

(22) Filed: Sep. 18, 2000

(30) Foreign Application Priority Data

Sep. 18, 1999 (DE) ............... 199 44 870

(51) Int. Cl.
*C12P 21/06* (2006.01)

(52) U.S. Cl. ..................................... 435/69.1

(58) Field of Classification Search ............... 435/69.2, 435/69.8, 252.33, 69.1; 530/324; 514/822; 930/10, 250, 300
See application file for complete search history.

(56) References Cited

U.S. PATENT DOCUMENTS

| | | | |
|---|---|---|---|
| 5,180,668 A | 1/1993 | Crause et al. | 435/69.2 |
| 5,286,714 A | 2/1994 | Crause et al. | |
| 5,316,947 A | 5/1994 | Crause et al. | |
| 5,389,529 A | 2/1995 | Panayotatos et al. | 435/69.8 |
| 5,616,476 A | 4/1997 | Crause et al. | |
| 5,652,139 A | 7/1997 | Wong et al. | 435/252.33 |
| 5,919,895 A | 7/1999 | Schmid et al. | 530/324 |

FOREIGN PATENT DOCUMENTS

| | | |
|---|---|---|
| EP | 0 324 712 A2 | 7/1989 |
| EP | 0 448 093 A2 | 9/1991 |
| EP | 0 511 393 A1 | 11/1992 |
| EP | 0 549 915 | 7/1993 |

OTHER PUBLICATIONS

Achstetter et al. A new signal peptide useful for secretion of heterologous proteins from yeast and its application for synthesis hirudin. (1992) Gene 110: 25-31.*
International Search Report, dated Feb. 28, 2001.
R. De Mot et al., "Homology of the root adhesion of *Pseudomonas fluorescens* OE 28.3 with porin F of *P. aeruginosa* and *P. syringae*," *Mol. Gen. Genet*, 231:489-493 (1992).
G. Braum and S.T. Cole, "DNA sequence analysis of the *Serratia marcescens ompA* gene: Implications for the organisation of an enterobacterial outer membrane protein," *Mol. Gen. Genet*, 195:321-328 (1984).
Sara L. Pealing et al., "Sequence of the Gene Encoding Flavocytochrome *c* from *Shewanella putrefaciens*: A Tetraheme Flavoenzyme That Is a Soluble Fumarate Reductase Related to the Membrane-Bound Enzymes from Other Bacteria," *Biochemistry*, 31:12132-12140 (1992).
esp@cenet summary for EP 0 549 915 published Jul. 7, 1993.

* cited by examiner

*Primary Examiner*—Tekchand Saidha
(74) *Attorney, Agent, or Firm*—Finnegan, Henderson, Farabow, Garrett & Dunner, L.L.P.

(57) ABSTRACT

The present invention relates to a efficient expression of a protein, particularly, hirudin; a protein precursor comprising a signal sequence and the sequence of $aa_X$-hirudin, wherein $aa_X$ is a selected amino acid, and $aa_X$ is preferably leucine; to its preparation and use; and to processes for finding signal sequences for secretory expression of any desired protein in *E coli*; and to processes for the secretory expression of any desired protein in *E coli*.

4 Claims, 1 Drawing Sheet

SEQUENCE LISTING

<160> NUMBER OF SEQ ID NOS: 33

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
tttttttaag cttgggctgc aggtc                                           25

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 2
tggcactggc aggtttcgct accgtagcgc aagcccttac gtatactgac tgca           54

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 3 tttttttgaat tcatgaaaaa gacagctatc gcattagcag tggcactggc aggtttc       57

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence: Primer

<400> SEQUENCE: 4
ggttctctta ttgccgctac ttctttcggc gttctggcac ttacgtatac tgactgca       58

<210> SEQ ID NO 5
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 5 tttttttgaat tcatgaaaaa caccttgggc ttggccattg gttctcttat tgccgc        56

<210> SEQ ID NO 6
<211> LENGTH: 61
<212> TYPE: DNA
<213> ORGANISM: Artificial Sequence
<220> FEATURE:
<223> OTHER INFORMATION: Description of Artificial Sequence: Primer

<400> SEQUENCE: 6
gttgccgtcg cagcgggcgt aatgtctgct caggcaatgg ctcttacgta tactgactgc    60
a                                                                    61

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 7
tttttTgaat tcatgatgat tactctgcgc aaacttcctc tggcggttgc cgtcgcagc      59

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Primer

<400> SEQUENCE: 8
ctaccctgat gggtaccgct ggtctgatgg gtaccgctgt tgctcttacg tatactgact      60
gca                                                                    63

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 9
tttttTgaat tcatgaaaaa aatgaacctg gctgtttgca tcgctaccct gatgggtacc      60

<210> SEQ ID NO 10
<211> LENGTH: 61
<212> TYPE: DNA
<213> ORGANISM: Artificial Sequence
<220> FEATURE:
<223> OTHER INFORMATION: Description of Artificial Sequence: Primer

<400> SEQUENCE: 10
ctgatcccgt tctttgcagc gttctgcctg ccggttttcg cgcttacgta tactgactgc      60
a                                                                      61

<210> SEQ ID NO 11
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 11
tttttTgaat tcatgtccat ccagcacttc gcgtcgccc tgatcccgtt ctttgc            56

<210> SEQ ID NO 12
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 12
gctgccgctg ctgttcaccc cggttaccaa agcgcttacg tatactgact gca              53

<210> SEQ ID NO 13
<211> LENGTH: 57

```
<212> TYPE: DNA
<213> ORGANISM: Artificial Sequence
<220> FEATURE:
<223> OTHER INFORMATION: Description of Artificial Sequence: Primer

<400> SEQUENCE: 13 tttttttgaat tcatgaaaca gtcgaccatc gcgctggcgc tgctgccgct gctgttc       57

<210> SEQ ID NO 14
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 14
gctgagctgc ctgatcaccc cggtgtccca ggcgcttacg tatactgact gca           53

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 15 tttttttgaat tcatgaaaca gagcgcgatc gcgctggctc tgctgagctg cctgatc      57

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Primer

<400> SEQUENCE: 16
ctttcgctga gtatggcgtt ggggatttca ctgcccgcat gggcacttac gtatactgac    60
tgca                                                                 64

<210> SEQ ID NO 17
<211> LENGTH: 65
<212> TYPE: DNA
<213> ORGANISM: Artificial Sequence
<220> FEATURE:
<223> OTHER INFORMATION: Description of Artificial Sequence: Primer

<400> SEQUENCE: 17 tttttttgaat tcatgaaatc gcggtacaaa cgtttgacct ccctggcgct ttcgctgagt   60
atggc                                                                65

<210> SEQ ID NO 18
<211> LENGTH: 55
<212> TYPE: DNA
<213> ORGANISM: Artificial Sequence
<220> FEATURE:
<223> OTHER INFORMATION: Description of Artificial Sequence: Primer

<400> SEQUENCE: 18
tggtttcagc tttagtaagc ggggttgcat ttgctcttac gtatactgac tgcac         55

<210> SEQ ID NO 19
<211> LENGTH: 60
<212> TYPE: DNA
<213> ORGANISM: Artificial Sequence
<220> FEATURE:
```

-continued

<223> OTHER INFORMATION: Description of Artificial Sequence: Primer

<400> SEQUENCE: 19
ttttgggaat tcatgaaaaa gacaattatg tctctggctg tggtttcagc tttagtaagc    60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 20
cggcgctgag tctcgcctta ttttctcacc tatcttttgc ccttacgtat actgactgca    60

<210> SEQ ID NO 21
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 21 tttttttgaat tcatgtcatt tcatcaccgg gtatttaaac tgtcggcgct gagtctc    57

<210> SEQ ID NO 22
<211> LENGTH: 227
<212> TYPE: DNA
<213> ORGANISM: Unknown Organism
<220> FEATURE:
<223> OTHER INFORMATION: Description of Unknown Organism:
      Hirudin-encoding DNA sequence
<221> NAME/KEY: CDS
<222> LOCATION: (1)..(195)

<400> SEQUENCE: 22 ctt acg tat act gac tgc act gaa tct ggt cag aac ctg tgc ctg tgc      48
Leu Thr Tyr Thr Asp Cys Thr Glu Ser Gly Gln Asn Leu Cys Leu Cys
 1               5                  10                  15 gaa gga tct aac gtt tgc ggc cag ggt aac aaa tgc atc ctt gga tcc      96
Glu Gly Ser Asn Val Cys Gly Gln Gly Asn Lys Cys Ile Leu Gly Ser
             20                  25                  30 gac ggt gaa aag aac cag tgc gtt act ggc gaa ggt acc ccg aaa ccg     144
Asp Gly Glu Lys Asn Gln Cys Val Thr Gly Glu Gly Thr Pro Lys Pro
         35                  40                  45 cag tct cat aac gac ggc gac ttc gaa gag atc cct gag gaa tac ctt     192
Gln Ser His Asn Asp Gly Asp Phe Glu Glu Ile Pro Glu Glu Tyr Leu
     50                  55                  60 cag taatagagct cgtcgacctg cagcccaagc tt                             227
Gln
 65

<210> SEQ ID NO 23
<211> LENGTH: 65
<212> TYPE: PRT
<213> ORGANISM: Unknown Organism
<220> FEATURE:
<223> OTHER INFORMATION: Description of Unknown Organism:
      Hirudin-encoded amino acid sequence

<400> SEQUENCE: 23

Leu Thr Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
             20                  25                  30

```
Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
 65

<210> SEQ ID NO 24
<211> LENGTH: 30
<212> TYPE: PRT
<213> ORGANISM: Unknown Organism
<220> FEATURE:
<223> OTHER INFORMATION: Description of Unknown Organism: Control:
      cgtase-Ala-hirudin

<400> SEQUENCE: 24

Met Lys Arg Asn Arg Phe Phe Asn Thr Ser Ala Ala Ile Ala Ile Ser
 1               5                  10                  15

Ile Ala Leu Asn Thr Phe Phe Cys Ser Met Gln Thr Ile Ala
            20                  25                  30

<210> SEQ ID NO 25
<211> LENGTH: 21
<212> TYPE: PRT
<213> ORGANISM: Serratia marcescens
<220> FEATURE:
<223> OTHER INFORMATION: Outer membrane protein

<400> SEQUENCE: 25

Met Lys Lys Thr Ala Ile Ala Leu Ala Val Ala Leu Ala Gly Phe Ala
 1               5                  10                  15

Thr Val Ala Gln Ala
            20

<210> SEQ ID NO 26
<211> LENGTH: 22
<212> TYPE: PRT
<213> ORGANISM: Pseudomonas fluorescens
<220> FEATURE:
<223> OTHER INFORMATION: oprF protein

<400> SEQUENCE: 26

Met Lys Asn Thr Leu Gly Leu Ala Ile Gly Ser Leu Ile Ala Ala Thr
 1               5                  10                  15

Ser Phe Gly Val Leu Ala
            20

<210> SEQ ID NO 27
<211> LENGTH: 25
<212> TYPE: PRT
<213> ORGANISM: Escherichia coli
<220> FEATURE:
<223> OTHER INFORMATION: lamB protein

<400> SEQUENCE: 27

Met Met Ile Thr Leu Arg Lys Leu Pro Leu Ala Val Ala Val Ala Ala
 1               5                  10                  15

Gly Val Met Ser Ala Gln Ala Met Ala
            20                  25

<210> SEQ ID NO 28
<211> LENGTH: 25
<212> TYPE: PRT
```

```
<213> ORGANISM: Shewanella putrefaciens
<220> FEATURE:
<223> OTHER INFORMATION: Fumarate reductase

<400> SEQUENCE: 28

Met Lys Lys Met Asn Leu Ala Val Cys Ile Ala Thr Leu Met Gly Thr
 1               5                  10                  15

Ala Gly Leu Met Gly Thr Ala Val Ala
            20                  25

<210> SEQ ID NO 29
<211> LENGTH: 23
<212> TYPE: PRT
<213> ORGANISM: Unknown Organism
<220> FEATURE:
<223> OTHER INFORMATION: Description of Unknown Organism: Beta -
      Lactamase/pBR322

<400> SEQUENCE: 29

Met Ser Ile Gln His Phe Arg Val Ala Leu Ile Pro Phe Phe Ala Ala
 1               5                  10                  15

Phe Ser Leu Pro Val Phe Ala
            20

<210> SEQ ID NO 30
<211> LENGTH: 21
<212> TYPE: PRT
<213> ORGANISM: Escherichia coli
<220> FEATURE:
<223> OTHER INFORMATION: Alk. phosphatase

<400> SEQUENCE: 30

Met Lys Gln Ser Thr Ile Ala Leu Ala Leu Leu Pro Leu Leu Phe Thr
 1               5                  10                  15

Pro Val Thr Lys Ala
            20

<210> SEQ ID NO 31
<211> LENGTH: 21
<212> TYPE: PRT
<213> ORGANISM: Escherichia fergusonii
<220> FEATURE:
<223> OTHER INFORMATION: Alk. phosphatase

<400> SEQUENCE: 31

Met Lys Gln Ser Ala Ile Ala Leu Ala Leu Leu Ser Cys Leu Ile Thr
 1               5                  10                  15

Pro Val Ser Gln Ala
            20

<210> SEQ ID NO 32
<211> LENGTH: 27
<212> TYPE: PRT
<213> ORGANISM: Paenibacillus macerans
<220> FEATURE:
<223> OTHER INFORMATION: Cyclodextrin glucanotransferase

<400> SEQUENCE: 32

Met Lys Ser Arg Tyr Lys Arg Leu Thr Ser Leu Ala Leu Ser Leu Ser
 1               5                  10                  15

Met Ala Leu Gly Ile Ser Leu Pro Ala Trp Ala
            20                  25

<210> SEQ ID NO 33
```

```
<211> LENGTH: 24
<212> TYPE: PRT
<213> ORGANISM: Salmonella typhimurium
<220> FEATURE:
<223> OTHER INFORMATION: Outer membrane protein

<400> SEQUENCE: 33

Met Ser Phe His His Arg Val Phe Lys Leu Ser Ala Leu Ser Leu Ala
 1               5                  10                  15

Leu Phe Ser His Leu Ser Phe Ala
            20
```

SIGNAL SEQUENCES FOR PREPARING LEU-HIRUDIN BY SECRETION BY *E. COLI* INTO THE CULTURE MEDIUM

The leech-derived product REFLUDAN® shows beneficial therapeutic properties in clinical trials (*Lancet*, 353, 429-438). Larger amounts of the product are therefore likely to be required in the future. The biologically active ingredient in the leech-derived product is [Leu$^1$, Thr$^2$]-63-desulfatohirudin, which is described in European patent 0 324 712, and which is hereinafter called "Leu-hirudin."

European patent 0 448 093 describes a process for preparing hirudin. The preferred embodiment of the patent comprises a hirudin whose N-terminal amino acid consists of alanine. Fusion of this hirudin to the signal sequence of α-cyclodextrin glycosyltransferase ("CGTase"), and transformation of an expression vector encoding this fusion protein, into an *E. coli* secretor mutant make it possible to prepare Ala-hirudin with crude yields of more than 2 grams per liter.

European patent 0 549 915 described variants of Ala-hirudin with improved stability. Preparation of these variants using the *E. coli* secretor system resulted in yields of several grams per liter. The yields are thus distinctly higher than the yields in the range of 4 mg per liter described by Dodt et al. for the hirudin variant HV1 after 24 hours of expression (*FEBS Letters* 202, 373-377 (1986)). Dodt et al. also describe that, while the main amount of hirudin is directed to the periplasm, only 29% of the material is found in the supernatant.

A negligible increase in the comparable yield (from 4 mg/L to 200-300 mg/L) is described in U.S. Pat. No. 5,573,929 by expressing the expression cassette via a pUC vector in a known manner in place of the pBR322-derived vector of Dodt et al. Bender et al. (*Appl. Microbiol. Biotechnol.* 34, 203-207 (1990)) describe the secretion of Thr-hirudin, which is described in European patent 0 171 024, by *Streptomyces lividans*. However, these yields compared with the yields obtained in European patents 0 448 093 and 0 549 915 (see above) are once again distinctly less. This also applies to expression in *E. coli* B as found by P. de Taxis du Poet et al. for secretion of the hirudin variant HV1 via the signal sequence Ompa of *E. coli*. The authors found yields of 300 mg/l hirudin in the periplasm and about 40 mg/l in the cell supernatant. The expression in insect cell systems, which is also described in the article, was low (400 μg/l).

Yields achieved with the yeast expression systems *Hansenula polymorpha* or *Pichia pastoris* come closest to the yields described in European patents 0 448 093 and 0 549 915, in contrast to the levels achieved with *S. cerevisiae*.

Rosenfeld et al. (*Protein Expression and Purification* 8, 476-482 (1996)) describe the expression and secretion of hirudin by the yeast *Pichia pastoris*. Yields of about 1.5 g/l of culture broth are achieved in this case. A similar order of magnitude can be achieved with the yeast *Hansenula polymorpha* (*Appl. Microbiol. Biotechnol.* 44, 377-385 (1995)). However, a considerable disadvantage of such expression systems is that the fermentation times are distinctly longer than for the *E. coli* system. It would thus be advantageous if Leu-hirudin could, like Ala-hirudin, be prepared by secretion by *E. coli*.

However, this is not possible with the system described in European patent 0 448 093, which proposes to extend the Leu-hirudin sequence by the tripeptide Ala-Thr-Arg to produce a pre-Leu-hirudin which is finally converted after reaction with trypsin into the native active ingredient Leu-hirudin. Following this proposal, a shaken flask experiment results in crude yields which are distinctly worse than described for Ala-hirudin. Thus, no distinct advantage is clearly evident compared with later yeast expression systems.

An object of the present invention is accordingly to prepare a fusion protein, wherein the combination of signal sequence and Leu-hirudin permits direct processing to Leu-hirudin and subsequent secretion of native Leu-hirudin in high yields by *E. coli*. This is prerequisite for developing a process which advantageously affects the costs of producing REFLUDAN®, both in the fermentation and in the subsequent purification, because of an improved initial hirudin concentration.

Surprisingly, it has now been found that signal sequences which permit direct secretion of Leu-hirudin by *E. coli* exist, and that the secretion is in fact more efficient than that described in European patent 0 448 093. The present invention therefore advantageously provides a process which makes large amounts of Leu-hirudin available without great expenditure.

Figure 1:
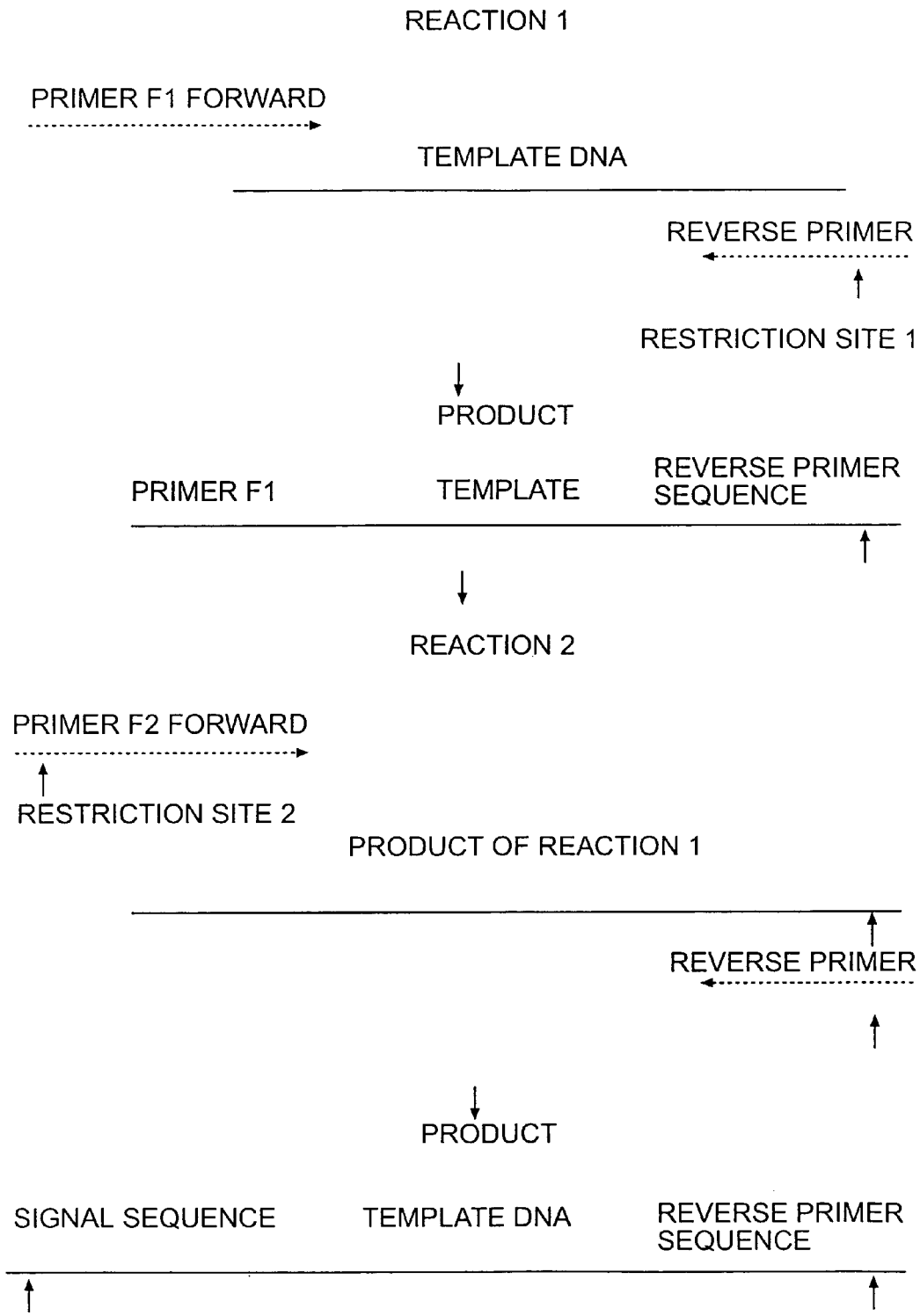
FIG. 1. An example reaction scheme for synthesizing a signal sequence.

In order to find advantageous signal sequences, the instant invention is directed to a method of PCR-assisted signal sequence screening. This method uses the DNA encoding the protein of interest as template, a defined reverse PCR primer, and variable forward primers which permit the synthesis of a DNA section which encodes a signal sequence coupled to a gene of interest. The reaction proceeds as shown in the scheme depicted in FIG. 1. It will be clear to the skilled worker that the number of reaction steps may vary according to the length of the signal sequence to be synthesized. Short signal sequences can be prepared with one reaction step, and longer sequences with two, three, or more reactions. In addition, the number of reactions depends on the apparatus used to synthesize the oligonucleotides used as primers.

The signal peptide gene fusion synthesized in this way can then be cleaved specifically with the enzymes recognizing restriction sites 1 and 2 (see FIG. 1), and then inserted into a correspondingly opened expression vector. The system becomes of general significance when hirudin is chosen as the gene or protein of interest. Moreover, variable selection of the N-terminal amino acid of hirudin is possible. Although this has a certain effect on the binding of hirudin to thrombin, i.e., will result in a change in the binding constant, the inhibitory effect of hirudin in relation to the thrombin activity remains measurable.

European patent EP 0 448 093 B1 describes the secretion of hirudin into the culture supernatant. The hirudin concentration therein can be determined directly via the well-known thrombin inhibition assay. The hirudin concentration is a direct measure of the efficiency of secretion and thus of the elimination of the signal sequence. EP 0 448 093 B1 describes, however, that, for example, hirudin starting with the amino acid leucine cannot be efficiently released into the supernatant via the signal sequence of the CGTase. It is now possible, using the method described above, to search for signal sequences which effectively permit this. Similarly, it is now possible to investigate the secretion of hirudins which start with any one of the other 19 amino acids. In each case, a spectrum of signal sequences results, the analysis of which permits, in a model way, the efficient processing of the carboxy-terminal amino acid of the signal peptide and the peptide residue attaching thereto.

The present invention therefore makes it possible to make a preselection of signal peptides for efficient secretion of any desired protein into the periplasm and thus increase the chances of developing an advantageous process for preparing a protein. The inventive process can be expedited or automated by shaking the transformation mixture of ligand mixture and competent cells as liquid culture in a selection medium overnight and, the next day, inoculating with an aliquot of the cells as described in Example 11. Innoculation of the cells into a medium which contains inducer to carry out the induction is followed by centrifuging most of the culture and freezing out the cell pellet. If activity of the desired protein is found upon expression, the corresponding expression plasmid can be re-isolated from the cells, linearized, and separated by gel electrophoresis from any autoligation products. The linear plasmid DNA is then religated and transformed anew into the host strain. It is then possible for individual colonies to be isolated and tested for their expression efficiency. It is possible to proceed in this case in such a way that the process meets the criteria of pharmaceutical approval.

A further advantage of the present inventive procedure is that it is easy to investigate different variants of a signal peptide, as arise in the course of evolution by exchange of amino acids between individual species, side by side for their ability to secrete a protein, such as hirudin, efficiently.

The process is also advantageous by comparison with the use of computer programs as described by Nielsen et al. (*Protein Engineering* 10, 1-6 (1997)), which predict cleavage sites between a signal sequence and a protein of interest. However, it is found that the predictions made therewith are not correct in every case, so that advantageous combinations may easily be overlooked. In addition, there is no relation between the prediction of correct processing and the actually achieved yield.

One aspect of the invention is a hirudin precursor comprising a signal sequence selected from the group comprising the signal sequences of the outer membrane protein of *Serratia marcescens*, the oprF protein of *Pseudomonas fluorescens*, the lamB protein of *Escherichia coli* (encoded by lambda receptor (lamB) gene) and the fumarate reductase of *Shewanella putrifaciens*, preferably selected from the group comprising the signal sequence of the outer membrane protein of *Serratia marcescens* and the fumarate reductase of *Shewanella putrifaciens*, for which there is C-terminal attachment of the sequence of Leu-hirudin.

Another aspect of the invention is a desired protein precursor comprising a signal sequence selected from the group comprising the signal sequences of the outer membrane protein of *Serratia marcescens*, the oprF protein of *Pseudomonas fluorescens*, the lamB protein of *Escherichia coli* (encoded by lambda receptor (lamB) gene) and the fumarate reductase of *Shewanella putrifaciens*, preferably selected from the group comprising the signal sequence of the outer membrane protein of *Serratia marcescens* and the fumarate reductase of *Shewanella putrifaciens*, for which there is C-terminal attachment of the sequence of Leu-hirudin.

Another aspect of the invention is a process for preparing Leu-hirudin, in which a hirudin precursor as described above occurs as intermediate, wherein
(a) an expression plasmid comprising a DNA sequence coding for the hirudin precursor is prepared;
(b) the expression plasmid from (a) is expressed in a suitable *E. coli* cell;
(c) the hirudin precursor is secreted from *E. coli* and simultaneously processed; and
(d) Leu-hirudin is isolated directly from the culture medium.

Likewise, another aspect of the invention is the use of a hirudin precursor as described above for preparing Leu-hirudin, preferably in a process as described above.

A further aspect of the invention is a process for finding a suitable signal peptide for secretory expression of any desired protein in *E. coli*, wherein
(a) hirudin or a hirudin derivative which has an antithrombotic effect and which has a defined amino acid $aa_X$ at its N terminus which is connected N-terminally to a signal peptide to be tested is expressed in *E. coli*;
(b) the expression rate is determined by measuring the hirudin activity in the culture supernatant;
(c) steps (a) and (b) are repeated with various signal peptides;
(d) a suitable signal peptide is selected by comparing the expression rates represented by the hirudin activities found in step (b).

Likewise, an aspect of the invention is the use of hirudin or a hirudin derivative which has an antithrombotic effect and which has a defined amino acid $aa_X$ at its N terminus for finding a signal peptide which makes it possible to secrete efficiently a precursor protein consisting of the signal peptide and any other desired protein with the N-terminal amino acid $aa_X$, with simultaneous elimination of the signal peptide from *E. coli*, in particular where $aa_X$ is leucine.

A further aspect of the invention is a process for preparing any desired protein by secretory expression in *E. coli*, wherein
(a) a suitable signal peptide is found by the process for finding a suitable signal peptide, e.g., by PCR assisted signal sequence screening;
(b) a nucleic acid construct coding for a precursor protein consisting of the suitable signal peptide from (a) and the desired protein is expressed in *E. coli*; and
(c) the desired protein is isolated from the culture supernatant, in particular where the N-terminal amino acid of the desired protein is leucine, and the expression takes place via a nucleic acid construct in which the sequence comprising the signal peptide codes for a signal peptide selected from the group comprising the outer membrane protein of *Serratia marcescens*, the oprF protein of *Pseudomonas fluorescens*, the lamB protein of *Escherichia coli*, and the fumarate reductase of *Shewanella putrifaciens*.

The synthesis of signal sequences which permit efficient synthesis and secretion of Leu-hirudin is described in the Examples. Likewise described is the synthesis of other signal sequences which did not lead to the objective or gave worse results in relation to the yield. The examples are intended in this connection to explain the concept of the invention on the basis of the selection of signal sequences on the basis of Leu-hirudin, but not to be considered as restricted thereto.

The described processes can be used for production of REFLUDAN®; described, for example, in Example 11.

EXAMPLE 1

Synthesis of a Fusion Gene Coding for a Fusion Protein Consisting of Leu-Hirudin and the Signal Sequence of the Outer Membrane Protein from *Serratia marcescens*

The expression plasmid used was the vector pJF118 which was described in European patent 0 468 539, in FIG. 1, because this is identical in its basic structure to the vector pCM7053 described in European patent 0 448 093.

The template used was the plasmid pK152 which is mentioned in Example 1 of European patent 0 448 093, which harbored the hirudin sequence corresponding to that shown in European patent 0 171 024.

The membrane protein was described by G. Braun and S. T. Cole (*Mol. Gen. Genet.* 195, 321-328 (1984)).

To synthesize the required DNA section, three oligonucleotide sequences were prepared.

Oligonucleotide hirrev has the sequence:

5' TTTTTTTAAG CTTGGGCTGC AGGTC 3' (SEQ ID NO: 1)

HindIII

The primer hybridizes with the region 227-210 bp of the hirudin gene depicted in Table 1.

Primer smompaf1 has the sequence:

5-TGGCACTGGC AGGTTTCGCT ACCGTAGCGC AAGCCcttac gtatactgac tgca-3' (SEQ ID NO: 2)

The primer hybridizes with nucleotides 1-19 of the hirudin sequence depicted in Table 1. The hybridizing part of the primer sequence is symbolized by small letters. The remainder of the sequence hybridizes with the region 229 bp-263 bp of the sequence published by G. Braun and S. T. Cole (*Mol. Gen. Genet.* 195, 321-328 (1984)).

Primer smompaf2 has the sequence:

5'-tttttttgaat tcATGAAAAA GACAGCTATC GCATTAGCAG TGGCACTGGC AGGTTTC-3' (SEQ ID NO: 3)

The primer sequence hybridizes from the 13 bp position onwards with the 201 bp-245 bp sequence published by Braun and Cole, and thus overlaps with the primer sequence smompaf2. The 1-12 position of the primer contains a recognition site for the restriction enzyme EcoRI and, adjoining, 6 T nucleotides in order to make recognition by the enzyme possible.

In a standard PCR (such as, for example, 94° C.: 10", 50° C.: 30", 72° C.: 45", 25 cycles) with DNA of the plasmid pK152, which harbors the sequence described in Table 1, as template, and the primers hirrev and smompaf1, the hirudin sequence was extended by the bacterial partial signal sequence. The reaction product was then reacted in a second PCR as template with the primers hirrev and smompaf2 under the same conditions. The reaction product was a DNA fragment which coded for a fusion protein which consisted of the hirudin sequence extended by the desired signal sequence. At the 5' end was the recognition site for the restriction enzyme EcoRI and at the 3' end was the recognition site for the enzyme HindIII.

The reaction product from the second PCR was reacted in a double-digestion mixture with the two restriction enzymes and was inserted as EcoRI/HindIII fragment into the vector DNA, which was opened with these two enzymes, in a T4 DNA ligase reaction. Competent cells of the *E. coli* strain Mc1061, or the secretor mutant WCM100, were transformed with the ligation mixture and grown under selection pressure on ampicillin-containing plates. The next morning, expression as described in Example 6 was then compared with Ala-hirudin expression using the *E. coli* strain WCM100/pCM7053. It was found that the expression obtained was about 1.5 times better than in the comparative test.

EXAMPLE 2

Synthesis of the Fusion Protein of Leu-Hirudin and the Signal Sequence of the oprF Gene Product from *Pseudomonas fluorescens*

Construction took place in accordance with the scheme described in Example 1 with the exception that, in place of the primers smompaf1/f2, two new primers were used which, in terms of their specificity for the hirudin gene and the sequence for recognition by the restriction enzyme EcoRI, had the same characteristics as the smompa primers but coded for the required signal sequence of the oprF gene (De, E. et al., *FEMS Microbiol. Lett.* 127, 267-272 (1995)).

Primer pfuf1 has the sequence:

5'-GGTTCTCTTA TTGCCGCTAC TTCTTTCGGC GTTCTGGCAc ttacgtatac tgactgca-3' (SEQ ID NO: 4)

Primer pfuf2 has the sequence:

5'-tttttttgaat tcatgAAAAA CACCTTGGGC TTGGCCATTG GTTCTCTTAT TGCCGC-3' (SEQ ID NO: 5)

In this case, the primer pfuf1 was used in accordance with Example 1 in PCR1 and primer pfuf2 was used correspondingly in PCR2. The expression was carried out by comparison with Ala-hirudin expression using the *E. coli* strain WCM100/pCM7053. The expression obtained was about 1.1 times better than in the comparative test. After fractionation by gel electrophoresis in the SDS-PAGE system, the hirudin band was isolated and the N-terminal sequence of the hirudin was determined. The sequence was completely intact and started with the amino acid leucine. This result was surprising because the program for identifying the putative signal peptidase recognition site predicted an extension of the hirudin by valine (Nielsen et al., *Protein Engineering* 10, 1-6 (1997)).

EXAMPLE 3

Synthesis of the Fusion Protein of Leu-Hirudin and the Signal Sequence of the lamB Gene Product from *E. coli*

Construction took place in accordance with the scheme described in Example 1 with the exception that, in place of the primers smompaf1/f2, two new primers were used which, in terms of their specificity for the hirudin gene and the sequence for recognition by the restriction enzyme EcoRI, had the same characteristics as the smompa primers but coded for the required signal sequence of the lamB gene (Clement, J. M. and Hofnung, M., *Cell* 27, 507-514 (1981)).

Primer lambbf1 has the sequence:

5'-GTTGCCGTCG CAGCGGGCGT AATGTCTGCT CAGGCAATGG CTcttacgta tactgactgc a-3' (SEQ ID NO: 6)

Primer lambbf2 has the sequence:

5'-tttttttgaat tcATGATGAT TACTCTGCGC AAACTTCCTC TGGCGGTTGC CGTCGCAGC-3' (SEQ ID NO: 7)

In this case, the primer lambbf1 1 was used in accordance with Example 1 in PCR1 and the primer lambbf2 was correspondingly used in PCR2. The expression was carried out by comparison with the Ala-hirudin expression using the *E. coli* strain WCM100/pCM7053. It was found that the expression obtained was at the same level as in the comparative test. After fractionation by gel electrophoresis in the SDS-PAGE system, the hirudin band was isolated, and the N-terminal sequence of the hirudin was determined. It was found that the sequence is completely intact and starts with the amino acid leucine. This result was surprising because the program for identifying the putative signal peptidase recognition site did not predict correct processing of hirudin.

EXAMPLE 4

Synthesis of the Fusion Protein of Leu-Hirudin and the Signal Sequence of the Precursor of Fumarate Reductase Flavoprotein Subunit from *Shewanella putrefaciens*.

Construction took place in accordance with the scheme described in Example 1 with the exception that, in place of the primers smompaf1/f2, two new primers were used, which, in terms of their specificity for the hirudin gene and the sequence for recognition by the restriction enzyme EcoRI, had the same characteristics as the smompa primers, but coded for the required signal sequence from Shewanella putrefaciens (Pealing S. L. et al.: Biochemistry 31, 12132-12140, (1992)). Since the publication described only the protein sequence, the amino acid sequence was translated in accordance with the codon tables into a DNA sequence so that the sequence which emerges for the primer spfccf1 is as follows:

5'-CTACCCTGAT GGGTACCGCT GGTCTGATGG GTACCGCTGT TGCTcttacg tatactgact gca-3' (SEQ ID NO: 8)

Primer spfccf2 has the sequence:

5'-tttttgaat tcATGAAAAA AATGAACCTG GCT-GTTTGCA TCGCTACCCT GATGGGTACC-3' (SEQ ID NO: 9)

In this case, the primer spfccf1 was used in accordance with Example 1 in PCR1 and primer spfccf2 was used correspondingly in PCR2. The expression was carried out by comparison with Ala-hirudin expression using the *E. coli* strain WCM100/pCM7053. It was found that the expression obtained is about 1.5 times better than in the comparative test. After fractionation by gel electrophoresis in the SDS-PAGE system, the hirudin band was isolated and the N-terminal sequence of the hirudin was determined. It was found that the sequence is completely intact and started with the amino acid leucine. This result was surprising, because the program for identifying the putative signal peptidase recognition site predicts processing on the carboxyl side of cysteine in position 6 of the hirudin sequence.

EXAMPLE 5

Synthesis of the Fusion Protein of Leu-Hirudin and the Signal Sequence of the β-Lactamase Precursor from pBR322

Construction took place in accordance with the scheme described in Example 1 with the exception that, in place of the primers smompaf1/f2, two new primers were used which, in terms of their specificity for the hirudin gene. and the sequence for recognition by the restriction enzyme EcoRI, had the same characteristics as the smompa primers but coded for the required signal sequence of the β-lactamase precursor protein (Sutcliffe J. G.; *Cold Spring Harbor Symp. Quant. Biol.* 43:77-90 (1978)).

Primer blatf1 has the following sequence:

5'-CTGATCCCGT TCTTTGCAGC GTTCTGCCTG CCG-GTTTTCG CGcttacgta tactgactgc a-3' (SEQ ID NO: 10)

Primer blatf2 has the sequence:

5'-tttttgaat tcATGTCCAT CCAGCACTTC CGCGTCGCCC TGATCCCGTT CTTTGC-3' (SEQ ID NO: 11)

In this case, the primer blatf1 was used in accordance with Example 1 in PCR1 and primer blatf2 was used correspondingly in PCR2. The expression was carried out by comparison with Ala-hirudin expression using the *E. coli* strain WCM100/pCM7053. It was found that the expression yield obtained is only 50%-90% of the yield obtained in the comparative test. After fractionation by gel electrophoresis in the SDS-PAGE system, the hirudin band was isolated and the N-terminal sequence of the hirudin was determined. It was found that the sequence is completely intact and starts with the amino acid leucine. This result was predicted by the program for identifying a putative signal peptidase recognition site.

EXAMPLE 6

Synthesis of the Fusion Gene of Leu-Hirudin and the Signal Sequence of the Precursor of Alkaline Phosphatase from *E. coli*

Construction took place in accordance with the scheme described in Example 1 with the exception that, in place of the primers smompaf1/f2, two new primers were used, which, in terms of their specificity for the hirudin gene and their sequence for recognition by the restriction enzyme EcoRI, had the same characteristics as the smompa primers but coded for the required signal sequence of the alkaline phosphatase protein from *E. coli* (Shuttleworth, H., Taylor, J. and Minton, N.; *Nucleic Acids Res.* 14 (21), 8689 (1986)).

Primer linkphoaf1 has the following sequence:

5'-GCTGCCGCTG CTGTTCACCC CGGTTACCAA AGCGcttacg tatactgact gca-3' (SEQ ID NO.: 12)

Primer linkphoaf2 has the sequence:

5'-tttttgAAT TCATGAAACA GTCGACCATC GCGCTG-GCGC TGCTGCCGCT GCTGTTC-3' (SEQ ID NO.: 13)

The two primers were optimized in terms of the codon choice for *E. coli*, i.e., they do not correspond entirely to the natural sequence of the starting gene.

In this case, the primer linkphoaf1 was used in accordance with Example 1 in PCR1 and primer linkphoaf2 was used correspondingly in PCR2. The expression was carried out by comparison with Ala-hirudin expression using the *E. coli* strain WCM100/pCM7053. It was found that the expression yield obtained was only a fraction of the yield obtained in the comparative test. After fractionation by gel electrophoresis in the SDS-PAGE system, the hirudin band was isolated and the N-terminal sequence of the hirudin was determined. It was found that the sequence was completely intact and started with the amino acid leucine. This result was predicted by the program for identifying the putative signal peptidase recognition site. However, the poor yield was surprising.

EXAMPLE 7

Synthesis of the Fusion Gene of Leu-Hirudin and the Signal Sequence of the Precursor of the Alkaline Phosphatase from *E. fergusonii*

Construction took place in accordance with the scheme described in Example 1 with the exception that, in place of the primers smompaf1/f2, two new primers were used, which, in terms of their specificity for the hirudin gene and their sequence for recognition by the restriction enzyme EcoRI, had the same characteristics as the smompa primers but coded for the required signal sequence of the alkaline phosphatase protein from *E. fergusonii* (Du Bose, R. F. and Hartl, D. L.; *Mol. Biol. Evol.* 7, 547-577 (1990)).

This signal sequence differs at five positions from the alkaline phosphatase from *E. coli*.

Primer fergusf1 has the following sequence:

5'-GCTGAGCTGC CTGATCACCC CGGTGTCCCA GGCGcttacg tatactgact gca-3' (SEQ ID NO.: 14)

Primer fergusf2 has the sequence:

5'-tttttttgaat tcATGAAACA GAGCGCGATC GCGCTG-GCTC TGCTgAGCTG CCTGATC-3' (SEQ ID NO.: 15)

The two primers were optimized in terms of the codon choice for *E. coli*, i.e., they did not correspond entirely to the natural sequence of the starting gene. In this case, the primer fergusf1 was used in accordance with Example 1 in PCR1 and primer fergusf2 was used correspondingly in PCR2. The expression was carried out by comparison with Ala-hirudin expression using the *E. coli* strain WCM100/pCM7053. It was found that the expression yield obtained was only a fraction of the yield obtained in the comparative test. It was a further approximately 50% lower than observed with the construct of signal peptide from *E. coli* alkaline phosphatase and Leu-hirudin.

EXAMPLE 8

Synthesis of the Fusion Gene of Leu-Hirudin and the Signal Sequence of the Precursor of Cyclodextrin Glucanotransferase from *Paenibacillus macerans*

Construction took place in accordance with the scheme described in Example 1 with the exception that, in place of the primers smompaf1/f2, two new primers were used, which, in terms of their specificity for the hirudin gene and their sequence for recognition by the restriction enzyme EcoRI, have the same characteristics as the smompa primers but code for the required signal sequence of the cyclodextrin glucanotransferase gene from *Paenibacillus macerans* (Takano, T., Fukuda, M., Monma, M., Kobayashi, S., Kainuma, K. and Yamane, K. J.; Bacteriol. 166, 1118-1122 (1986)).

Primer baccdgf1 has the following sequence:

5'-CTTTCGCTGA GTATGGCGTT GGGGATTTCA CTGCCCGCAT GGGCActtac gtatactgac tgca-3' (SEQ ID NO.: 16)

Primer baccdgf2 has the sequence:

5'-tttttttgaat tcATGAAATC GCGGTACAAA CGTTTGACCT CCCTGGCGCT TTCGCTGAGT ATGGC-3' (SEQ ID NO.: 17)

In this case, the primer baccdgf1 was used in accordance with Example 1 in PCR1 and primer baccdgf2 was used correspondingly in PCR2. The expression was carried out by comparison with Ala-hirudin expression using the *E. coli* strain WCM 100/pCM7053. It was found that the expression yield obtained was about one quarter of the yield obtained in the comparative test. The synthesized hirudin behaved like Leu-hirudin in the thrombin inhibition assay, indicating that the signal peptide was correctly processed. This did not correspond to the expectation deduced from the theoretical analysis, which indicated an extension of 8 amino acids or, alternatively, a truncation by two amino acids at the N-terminus.

EXAMPLE 9

Synthesis of the Fusion Gene from Leu-Hirudin and the Signal Sequence of the *E. coli* PCFO20 Fimbrillin Precursor Protein (fotA)

Construction took place in accordance with the scheme described in Example 1 with the exception that, in place of the primers smompaf1/f2, two new primers were used, which, in terms of their specificity for the hirudin gene and their sequence for recognition by the restriction enzyme EcoRI, had the same characteristics as the smompa primers but coded for the required signal sequence of the *E. coli* PCFO20 fimbrillin precursor protein (Viboud, G. I., Jonson, G., Dean-Nystrom, E. and Svennerholm, A. M.; Infect. Immun. 64 (4), 1233-1239 (1996)).

Primer pcf1-ala has the following sequence:

5'-TGGTTTCAGC TTTAGTAAGC GGGGTTGCAT TTGCTCTTAC GTATACTGAC TGCAC-3' (SEQ ID NO.: 18)

Primer p-pcf2 has the sequence:

5'-TTTTGGGAAT TCATGAAAAA GACAATTATG TCTCTGGCTG TGGTTTCAGC TTTAGTAAGC-3' (SEQ ID NO.: 19)

In this case, the primer pcf1-ala was used in accordance with Example 1 in PCR1 and the primer p-pcf2 was used correspondingly in PCR2. The expression was carried out by comparison with the Ala-hirudin expression using the *E. coli* strain WCM100/pCM7053. It was found that the expression yield obtained was about 40% of the yield obtained in the comparative test.

EXAMPLE 10

Synthesis of the Fusion Gene of Leu-Hirudin and the Signal Sequence of *S. typhimurium* Outer Membrane Protein (fimD)

Construction took place in accordance with the scheme described in Example 1 with the exception that, in place of the primers smompaf1/f2, two new primers were used, which, in terms of their specificity for the hirudin gene and their sequence for recognition by the restriction enzyme EcoRI, had the same characteristics as the smompa primers but coded for the required signal sequence of the *S. typhimurium* outer membrane protein (Rioux, C. R., Friedrich, M. J. and Kadner, R. J.; J. Bacteriol. 172 (11), 6217-6222 (1990)).

Primer styfimf1 has the following sequence:

5'-CGGCGCTGAG TCTCGCCTTA TTTTCTCACC TATCTTTTGC Ccttacgtat actgactgca-3' (SEQ ID NO.: 20)

Primer styfimf2 has the sequence:

5'-tttttttgaat tcaTGTCATT TCATCACCGG GTATTTAAAC TGTCGGCGCT GAGTCTC-3 (SEQ ID NO.: 21)

In this case, the primer styfimf1 was used in accordance with Example 1 in PCR1 and the primer styfimf2 was used correspondingly in PCR2. The expression was carried out by comparison with the Ala-hirudin expression using the *E. coli* strain WCM100/pCM7053. It was found that the expression yield obtained was about 10% of the yield obtained in the comparative test.

EXAMPLE 11

Expression in E. coli

This example describes expression of hirudin. For this purpose, 1-5 ml portions of LB medium which contains 25 mg/ml ampicillin and 0.5-2 mM IPTG (isopropyl β-D-thiogalactopyranoside) were inoculated with cells of a transformant and shaken at 220 rpm in an incubating shaker at 28° C. for about 20 hours. Subsequently, after optical density determination, the cell suspension was centrifuged and hirudin was determined in the clear supernatant.

Expression of the Ala-hirudin described in European patent 0 448 093 via the plasmid pCM7053 in the secretor mutant WCM100 described in the patent was carried out in parallel with expression of REFLUDAN®. This makes direct comparison of the expression rate possible.

Expression on a larger scale can take place as described in U.S. Pat. No. 5,616,476. REFLUDAN® can then be purified by the methods described in Examples 5 and 6 in described above.

EXAMPLE 12

Determination of the Hirudin Concentration

Determination of hirudin concentration was carried out by the method of GrieBbach et al. (*Thrombosis Research* 37, 347-350 (1985)). For this purpose, defined amounts of a REFLUDAN® standard were included in the series of measurements to construct a calibration plot. It was thus possible to state the yield directly in mg/l.

TABLE 1

Hirudin-encoding DNA sequence (SEQ ID NO:22) with translation into amino acids (SEQ ID NO:23)

```
CTTACGTATACTGACTGCACTGAATCTGGTCAGAACCTGTGCCTGTGCGAAGGATCTAAC   60
 L  T  Y  T  D  C  T  E  S  G  Q  N  L  C  L  C  E  G  S  N    -

GTTTGCGGCCAGGGTAACAAATGCATCCTTGGATCCGACGGTGAAAAGAACCAGTGCGTT  120
 V  C  G  Q  G  N  K  C  I  L  G  S  D  G  E  K  N  Q  C  V    -

ACTGGCGAAGGTACCCCCGAAACCGCAGTCTCATAACGACGGCGACTTCGAAGAGATCCCT  180
 T  G  E  G  T  P  K  P  Q  S  H  N  D  G  D  F  E  E  I  P    -

GAGGAATACCTTCAGTAATAGAGCTCGTCGACCTGCAGCCCAAGCTT               227
 E  E  Y  L  Q  *  *------------------------------              -
```

TABLE 2

| Ex. | Signal sequence | Primary structure | Relative yield per ml of culture | SEQ ID NO.: |
|---|---|---|---|---|
| — | Control: cgtase-Ala-hirudin | MKRNRFFNTS AAIAISIALNTFF CSMQTIA | 1 | 24 |
| 1 | Outer membrane protein/ *Serratia marcescens* | MKKTAIALAVALAGFATVAQ A | 1.5 | 25 |
| 2 | oprF protein/ *Pseudomonas fluorescens* | MKNTLGLAIGSLIAATSFGV LA | 1.1 | 26 |
| 3 | lamB protein/*E. coli* | MMITLRKLPL AVAVAAGVMS AQAMA | 1 | 27 |
| 4 | Fumarate reductase/ *Shewanella putrifaciens* | MKKMNLAVCI ATLMGTAGLM GTAVA | 1.5 | 28 |
| 5 | β-Lactamase/pBR322 | MSIQHFRVAL IPFFAAFSLPVFA | 0.5 | 29 |
| 8 | Alk. phosphatase/*E. coli* | MKQSTIALAL LPLLFTPVTK A | 0.1 | 30 |
| 9 | Alk. phosphatase/*E. fergusonii* | MKQSAIALAL LSCLITPVSQ A | 0.05 | 31 |
| 10 | Cyclodextrin glucanotransferase/ *Paenibacillus macerans* | MKSRYKRLTS LALSLSMALGI SLPAWA | 0.25 | 32 |
| 11 | Outer membrane protein/ *S. typhimurium* | MSFHHRVFKL SALSLALFSH LSFA | 0.11 | 33 |

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

We claim:

1. A process for selecting a signal peptide for secretory expression of a desired hirudin or hirudin derivative protein in *E. coli*, comprising:
   (a) expressing in *E. coli* in culture medium, hirudin or a hirudin derivative which has antithrombotic activity, and which has a defined amino acid, $aa_x$, at its N terminus, wherein said amino acid is connected via its N-terminal to a test signal peptide;
   (b) determining expression rate by measuring said hirudin or hirudin derivative activity in the culture supernatant;
   (c) repeating steps (a) and (b) with various signal peptides;
   (d) selecting said signal peptide by comparing the expression rates represented by the hirudin or hirudin derivative antithrombotic activity found in step (b) wherein the *E. coli* bacteria are not *E. coli* secretor mutants.

2. The process of claim 1, wherein $aa_x$ is leucine.

3. The process of claim 1, further comprising expressing said signal peptide and the desired hirudin or hirudin derivative protein in *E. coli* via a nucleic acid construct, wherein expression of the desired hirudin or hirudin derivative protein and said signal peptide occurs with simultaneous elimination of said signal peptide wherein the *E. coli* bacteria are not *E. coli* secretor mutants.

4. The process of claim 1, wherein the desired hirudin or hirudin derivative protein is hirudin.

* * * * *

UNITED STATES PATENT AND TRADEMARK OFFICE
CERTIFICATE OF CORRECTION

PATENT NO. : 7,455,987 B1  Page 1 of 1
APPLICATION NO. : 09/664326
DATED : October 20, 2009
INVENTOR(S) : Paul Habermann et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 737 days.

should read (*) Notice: Subject to any disclaimer, the term of this patent is extended or adjusted under 35 U.S.C. 154(b) by 736 days.

Signed and Sealed this

Third Day of August, 2010

David J. Kappos
*Director of the United States Patent and Trademark Office*